US00PP20486P2

(12) United States Plant Patent
Lim

(10) Patent No.: US PP20,486 P2
(45) Date of Patent: Nov. 17, 2009

(54) FLORIBUNDA ROSE PLANT NAMED 'BAISUHE'

(50) Latin Name: *Rosa hybrida*
Varietal Denomination: BAIsuhe

(75) Inventor: Peter P. Lim, McMinnville, OR (US)

(73) Assignee: Bailey Nurseries, Inc., St. Paul, MN (US)

( * ) Notice: Subject to any disclaimer, the term of this patent is extended or adjusted under 35 U.S.C. 154(b) by 0 days.

(21) Appl. No.: 12/228,999

(22) Filed: Aug. 19, 2008

(51) Int. Cl.
*A01H 5/00* (2006.01)

(52) U.S. Cl. ..... Plt./151
(58) Field of Classification Search ..... Plt./151
See application file for complete search history.

*Primary Examiner*—Annette H Para
(74) *Attorney, Agent, or Firm*—Penny J. Aguirre

(57) ABSTRACT

A new cultivar of floribunda rose, *Rosa* 'BAIsuhe', characterized by its clusters of fragrant, fully double hybrid tea-shaped flowers that are medium red in color suffused with pink highlights as they mature, its dark red flower buds, its everblooming flowering habit, its medium green satiny foliage that is resistant to rose blackspot and powdery mildew, and its rounded and compact plant habit. The new variety is readily propagated on its own roots and hardy in U.S.D.A. Zones 4 to 9.

2 Drawing Sheets

Botanical classification: *Rosa hybrida.*
Variety denomination: 'BAIsuhe'.

BACKGROUND OF THE INVENTION

The present invention relates to a new and distinct cultivar of *Rosa hybrida.* The new cultivar will be referred to hereafter by its cultivar name, 'BAIsuhe'. 'BAIsuhe' is a floribunda rose suitable for landscape plantings.

The new cultivar of shrub rose is a selection from a controlled breeding program conducted by the inventor in Yamhill, Oreg. with a focus to create cultivars of roses with greater winter hardiness and improvements in disease resistance combined with good flower quality.

The new variety of floribunda rose, 'BAIsuhe', designated as seedling No. 96A723-1R was selected among seedlings derived from a cross made in Yamhill, Oreg. in 1996 between the hybrid tea cultivar 'Silver Jubilee' (not patented) as the female parent and an unnamed proprietary seedling of the inventor's, No. 93A254, as the male parent. 'BAIsuhe' was budded onto understock in 1996 and selected by the inventor as unique for its distinct characteristics in summer of 1999.

The new cultivar has been asexually propagated by budding and rooting of softwood cuttings from a plant grown on its own roots in Yamhill, Oreg. Asexual propagation determined that the characteristics of this cultivar are stable and are reproduced true to type in successive generations.

SUMMARY OF THE INVENTION

The following traits have been repeatedly observed and represent the characteristics of the new rose as observed for a period of seven years in Yamhill, Oreg., St. Paul, Minn. and several other test sites in the U.S. These attributes in combination distinguish 'BAIsuhe' as a unique cultivar of rose.

1. 'BAIsuhe' exhibits clusters of fully double hybrid tea-shaped flowers that are medium red in color and suffused with pink as they mature. The flower buds of 'BAIsuhe' are dark red in color. 'BAIsuhe' is classified as a medium red by American Rose Society standards.

2. 'BAIsuhe' has fragrant flowers with a medium rose scent.
3. 'BAIsuhe' exhibits a compact rounded habit with a height of 90 cm to 1.5 m.
4. 'BAIsuhe' exhibits medium green, satiny foliage.
5. 'BAIsuhe' exhibits an everblooming habit.
6. 'BAIsuhe' has shown excellent resistance to rose blackspot (*Diplocarpon rosae*) and powdery mildew (*Sphaerotheca pannosa* var. *rosa*).
7. 'BAIsuhe' is hardy in U.S.D.A. Zones 4 to 9.
8. 'BAIsuhe' is a vigorous grower and readily propagated by softwood cuttings and grown on its own roots.

The new cultivar of shrub rose can be readily distinguished from its parents and other cultivars. The female parent, 'Silver Jubilee', is a hybrid tea rose with very large glossy foliage and very large fully double flowers that are light golden yellow in color. The male parent, seedling No. 93A254 has double (not fully double) red flowers that are smaller in size than those of 'BAIsuhe'. The cultivars 'BAIhero' (U.S. Plant Pat. No. 15,400) and 'John Franklin' (not patented) are close comparison roses. They both have similarity to 'BAIsuhe' in having double medium red hybrid tea-shaped flowers. 'BAIhero' differs from 'BAIsuhe' in having lighter green foliage and larger flowers that have less petals, are less fragrant, and mature to a pinker color in comparison to 'BAIsuhe'. 'John Franklin' differs from 'BAIsuhe' in having foliage with a matte surface, flowers that have frilly petals and mature to a deep pink color, pinker flower buds, an upright rounded plant habit, and a recurrent blooming habit.

BRIEF DESCRIPTION OF THE DRAWING

The accompanying colored photographs illustrate the overall appearance and distinct characteristics of the new floribunda rose, 'BAIsuhe', as grown outdoors in trial blocks and containers in St. Paul, Minn. and Yamhill, Oreg. The photographs were taken of four year-old plants grown on their own roots.

Figure 1:
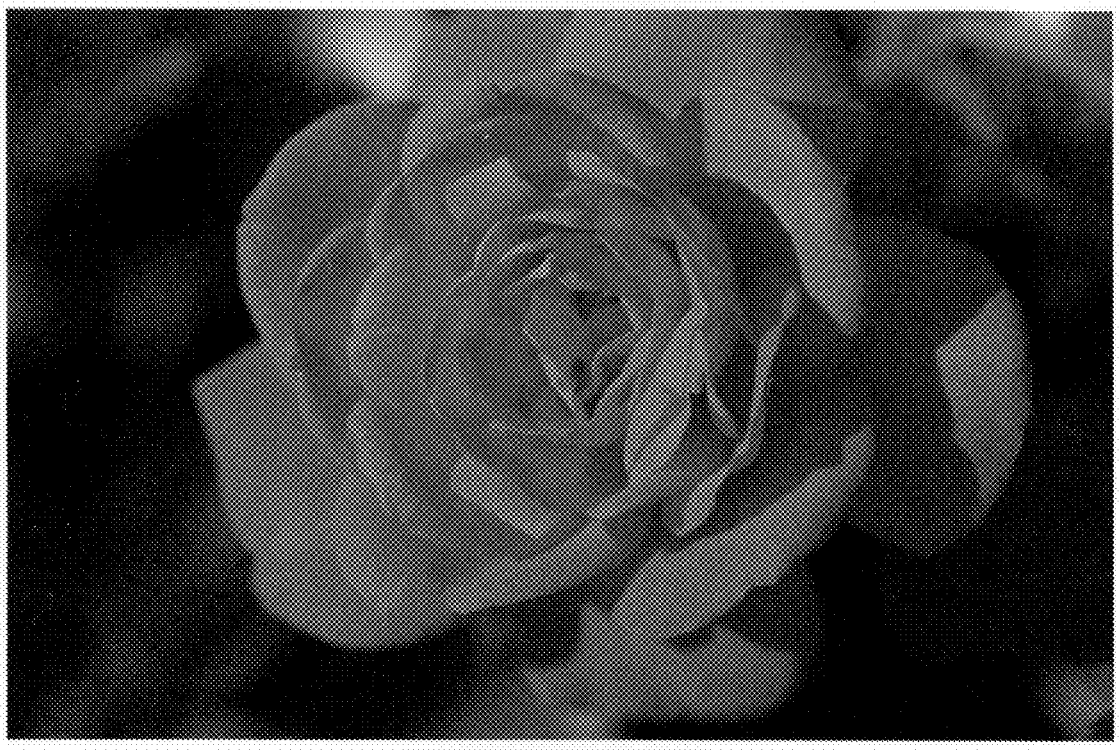
FIG. 1 provides a close-up view of a fully open flower of 'BAIsuhe'.
Figure 2:
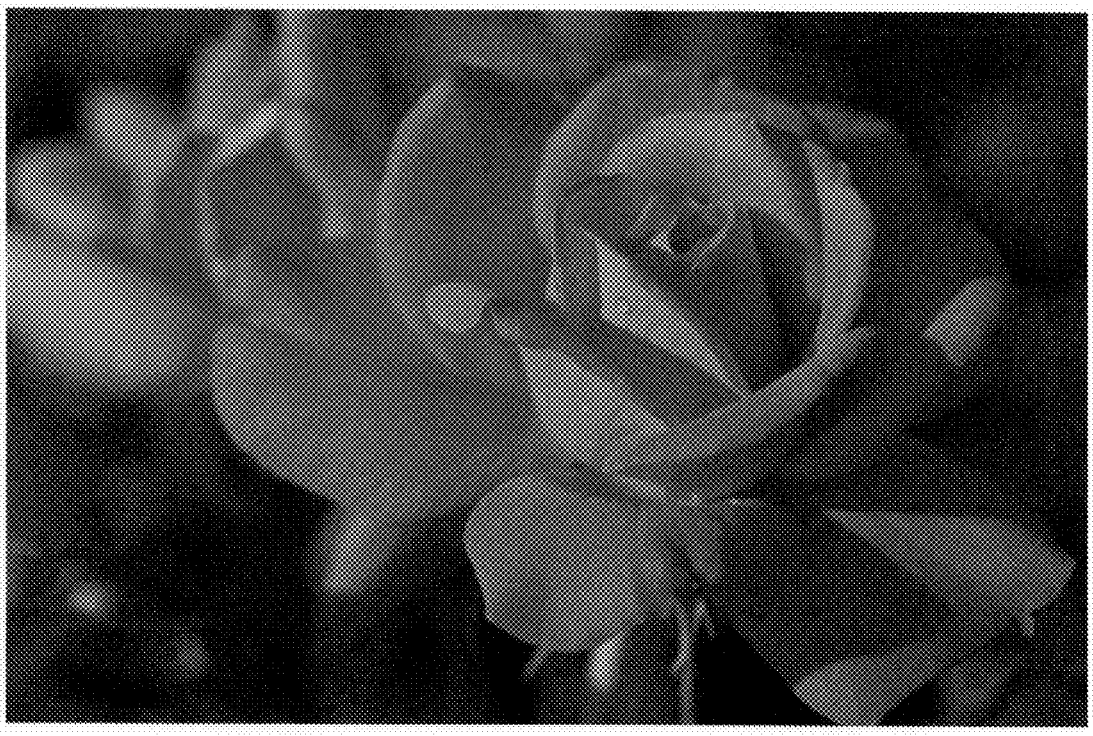
FIG. 2 provides a close-up view of newly opened flower of 'BAIsuhe'.
Figure 3:
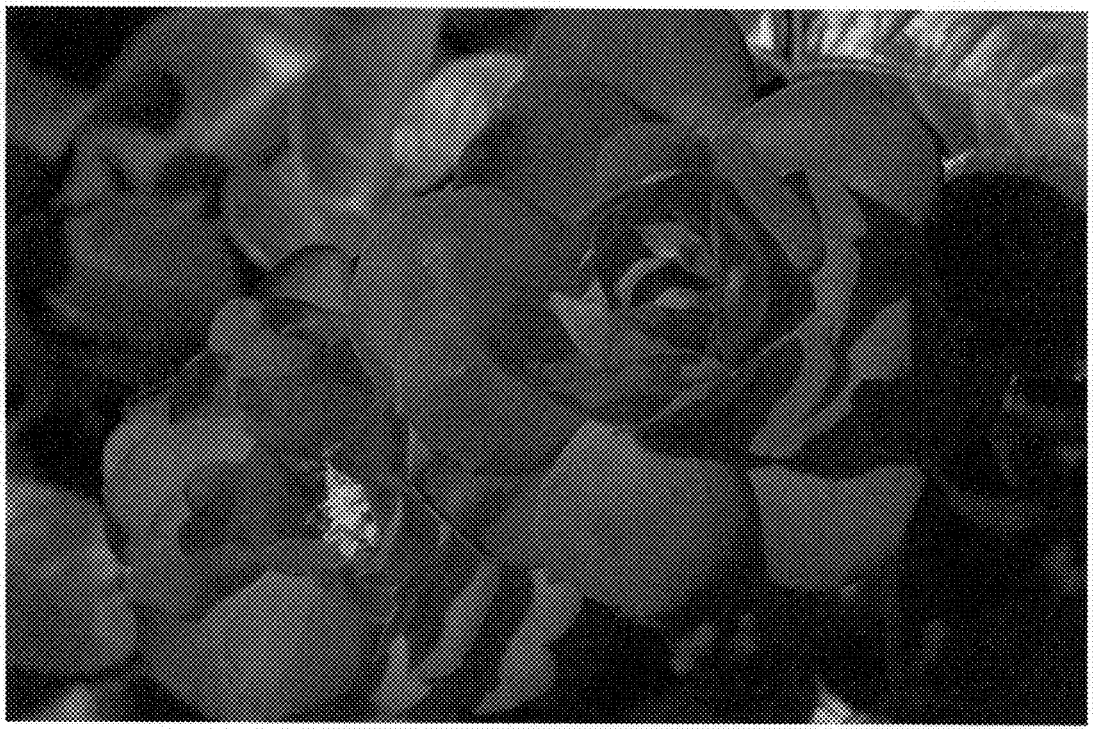
FIG. 3 provides a close-up view of a fully open flower of 'BAIsuhe' on the right and a mature flower of 'BAIsuhe' on the left.

The colors in the photographs are as close as possible with digital photography techniques available, the color values cited in the detailed botanical description accurately describe the colors of the new shrub rose.

DETAILED BOTANICAL DESCRIPTION

The following is a detailed description of the new cultivar as observed on three year-old container plants and seven year-old field-grown plants as grown outdoors in Yamhill, Oreg. and St. Paul, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming habit.*—Everblooming throughout the growing season.

*Plant habit.*—Compact and rounded.

*Height and spread.*—Reaches 90 cm to 1.5 m in height and about 1 M in spread.

*Cold hardiness.*—U.S.D.A. Zone 4 to 9.

*Diseases and pests.*—High degree of resistance observed to rose blackspot (*Diplocarpon rosae*) and powdery mildew (*Sphaerotheca pannosa* var. *rosa*).

*Propagation.*—Softwood stem cuttings, own roots.

*Growth.*—Vigorous and strong.

Branch description:

*Stem color.*—Young; 144B, maturing; between 144A, mature wood; N199B with areas showing through of N199C.

*Stem surface.*—Young and mature; glabrous, adult wood; mostly glabrous with bark-like ridges.

*Stem size.*—Average of 4 mm in width, up to 95 cm in length, an average of 8 mm in width.

*Thorns.*—Triangular, held horizontal to slightly downward, straight apex, oval base, average of 4 mature thorns per 5 cm in number, an average of 4.5 mm in length with a base 5 mm in length and 2 mm in width, color is 160B with 165B toward the tip to solid 165B.

*Branching habit.*—Produces an average of 3 lateral breaks in whorl is pruned.

Foliage description:

*Leaves.*—Division is odd-pinnate, average of 9 cm in length and 6.5 cm in width, internode length is an average of 2.5 cm.

*Leaflets.*—Typically 5 (less often 3 or 7), broadly ovate in shape, rounded base, broadly acute to cuspidate apex, serrated margins, surface when young is glabrous and glossy on upper surface and glabrous and dull on lower surface, surface when mature is glabrous and satiny on upper surface and finely puberlent lower surface, average of 2.5 cm in length and 3 cm in width, color: young leaves upper surface; 144A suffused with and margins N77A, young leaves lower surface; 166A turning to 144A suffused with 176A, mature leaves upper surface; darker than 139A, mature leaves lower surface; 138A.

*Rachis.*—Average of 6 cm in length and 1.5 mm in diameter, color of upper surface 146B with 144A between ridges, color of lower surface 144A.

*Stipules.*—Long and narrow with auricle facing outward, adnate to petiole, average of 1 cm in length and 4 mm in width with leafy tips on apex 3 mm in length and 1 mm in width, color of upper surface is 144A on margins, 144B near center and 144D on middle ridge, color of lower surface is 144A on margins and 144B in centers.

*Petioles.*—Very short (appears sessile), average of 1 mm in length and diameter, color of upper surface 146B, color of lower surface 144A.

Inflorescence description:

*Inflorescence type.*—Clusters of fully double hybrid tea-shaped flowers.

*Flower number.*—Average of 4 per lateral stem.

*Flower fragrance.*—Medium rose scent.

*Flower longevity.*—About 3 to 5 days, depending on temperature and sunlight exposure.

*Flower type.*—Fully double, hybrid tea-shaped.

*Flower size.*—Average of 8 cm in diameter and 4.5 cm in depth (to a bottom of sepal tips).

*Peduncles.*—Stiff, average of 3.5 cm in length and 3 mm in diameter, 144A in color, surface is glabrous.

*Bracts.*—Typically 0 to 1 per flower, if present; average of 3 cm in length and 3 mm in width, lanceolate in shape, sharply serrated margins, apex is acute with leaf-like tip, truncate base, sessile, color of upper surface 137B to 137C with base 144A, color of lower surface 137A with base 145D.

*Flower buds.*—Ovate in shape, medium in size with an average of 3 cm in length and 2.5 cm in width prior to opening, blend of 63A and 63B in color, texture is glabrous.

*Sepals.*—5, broadly lanceolate in shape, margin is entire on 2 and foliaceous with glandular appendages in irregular or pinnate pattern on 3, color of upper surface is 138B with centers 144B and overlay and margins 196C, color of lower surface is 138A with margins 196C, upper surface is tomentose, lower surface is glabrous with some glands, average of 2.3 cm in length and 7.5 mm in width, apex is apiculate to leaf-like, base is truncate, aspect is upright in bud stage changing to horizontal when bud opens and reflexed in full bloom.

*Petals.*—35–40, drop readily and cleanly, broadly obovate in shape with some irregular in shape (almost kidney-shaped) and rolled to almost cone-like, upper surface is glabrous and lower surface is glabrous and satiny, entire margin, cuneate base, rounded apex, average of 4 cm in length and 3.5 cm in width, color: opening flowers upper surface; 46A blended with 46D towards base, opening flowers lower surface; blend of 63A and 63B, fully open flowers upper surface; N66A suffused with N66C, fully open flowers lower surface; N66C suffused with N66D, end of bloom upper surface (changes just before petal drop); blend of 71A and 71B, end of bloom lower surface; blend of 71B and 70B, petal spot; 11D with 11C at base.

*Receptacle.*—Average of 8 mm in diameter and 9 mm in depth when flower is fully open, urn shaped, glabrous and satiny, 144A in color.

*Pistils.*—Average of 38, stigma is an average of 0.5 mm in length, an average of 1 mm in width and matures to 145D in color, style is an average of 1 cm in length and 162D in color with shadings of 165A, ovary is 2 mm in length and 1 mm width, 155A in color and pilose with very fine hairs about 2 mm in length.

*Stamens.*—About 80 with a few additional without anther or petaloid, curved inward towards pistils, filaments are an average of 6 mm in length and 162D in color, anthers are an average of 1.5 mm in length, an average of 1 mm in width and 162D in color, pollen is abundant and 165A in color.

*Hips.*—Due to its everblooming habit, hips were not observed to mature prior to frost on the plants observed for data collection.

It is claimed:

1. A new and distinct cultivar of floribunda rose plant named 'BAIsuhe' as herein illustrated and described.

* * * * *